United States Patent [19]
Clark et al.

[11] Patent Number: 5,705,648
[45] Date of Patent: Jan. 6, 1998

[54] MEPIQUAT CHLORIDE

[75] Inventors: Richard U. Clark, Knoxville, Tenn.; James S. Lovell; James C. Thigpen, both of Summerton, S.C.; David William Bristol; John Raymond Tyndall, both of Pisgah Forest, N.C.; Albert Roger Frisbee, Hendersonville, N.C.

[73] Assignee: Micro Flo Co., Mulberry, Fla.

[21] Appl. No.: 325,945

[22] Filed: Oct. 17, 1994

Related U.S. Application Data

[63] Continuation of Ser. No. 894,366, Jun. 4, 1992, abandoned.
[51] Int. Cl.$^6$ .................................................. C07D 211/14
[52] U.S. Cl. ........................................... 546/349; 424/408
[58] Field of Search ................................. 546/184, 349; 424/408

[56] References Cited

U.S. PATENT DOCUMENTS

| | | | |
|---|---|---|---|
| 3,277,118 | 10/1966 | Schmid et al. | 549/492 |
| 3,905,798 | 9/1975 | Zeeh et al. | 504/177 |
| 5,468,720 | 11/1995 | Lisa et al. | 504/236 |

OTHER PUBLICATIONS

Sommer, H.Z. et al, J. Org. Chem. 1971, 36(6), pp. 824–828.
Nosko, S. "Economical Aspects of Solvent Recycling" LaborPraxis, 1991, 15(9), pp. 723–724, 726, 728–730, 730, 734, abstract only.
Croxall, W.J. et al, "Benzyltrimethylammonium Ethoxide" Organic Synthesis, 1963, pp. 98–101.
PIX, BASF Corporation, Parsippany, NJ, (1989).

*Primary Examiner*—C. Warren Ivy
*Assistant Examiner*—Garth M. Dahler
*Attorney, Agent, or Firm*—Banner & Witcoff

[57] ABSTRACT

Mepiquat chloride is formed from the reaction between N-methylpiperidine and chloromethane in an anhydrous liquid solvent selected from the group consisting of acetone, methyl ethyl ketone, toluene, tetrahydrofuran, isopropanol, acetonitrile, N,N-dimethylformamide and methylene chloride in the absence of sodium hydroxide. Mepiquat chloride precipitates as a solid of high purity and is recovered under a substantially moisture-free atmosphere.

The solid mepiquat chloride can be sealed into a water soluble pouch or into a water soluble encapsulated solid form (e.g., granule, pellet, or briquette) for convenient handling. The pouch contains powdered mepiquat chloride or the encapsulated solid is merely introduced directly into a spray tank or reservoir for application with low human exposure and no containers in contact with the mepiquat chloride that require disposal.

Mepiquat chloride is used as a component of a system for growing a number of commodity plants including cotton. The first component is a plant growth regulator applied to at least one of: (a) a furrow for cotton plant seeds, (b) to a cotton plant bearing the first true leaves, (c) to a cotton plant at pinhead square, and (d) to a cotton plant at early bloom. The plant growth regulating agents produce higher plant masses with high levels of boll retention. At mid-bloom, mepiquat chloride is applied to retard vegetative growth in favor of fruit (boll) production.

28 Claims, No Drawings

MEPIQUAT CHLORIDE

This application is a continuation-in-part of U.S. application Ser. No. 07/894,366, filed Jun. 4, 1992, now abandoned, the disclosure of which is herein incorporated by reference.

FIELD OF THE INVENTION

The invention relates to the manufacture, packaging, and use of mepiquat chloride.

BACKGROUND OF THE INVENTION

Mepiquat chloride (N,N-dimethylpiperidinium chloride) is used annually as the active ingredient for controlling excessive vegetative growth on millions of acres of cotton, potatoes, sweet potatoes, peanuts, grapes, corn, wheat, citrus, tomatoes, and onions. The desired growth stunting effects are particularly desired when the crop is grown in fertile soil or after weather conditions that favor plant growth rather than fruit production.

Mepiquat chloride has traditionally been made in a basic aqueous solution (maintained with NaOH) by adding two methyl groups to the ring nitrogen atom in piperidine by contacting an aqueous solution containing piperidine with chloromethane in a molar ratio of about 2:1 chloromethane to piperidine at a pressure of about 95–100 psi. This dimethylation process yields about 50–60% mepiquat chloride in aqueous solution. A wash is used to remove the NaCl by-product of the reaction to a level of about 1 wt % NaCl. Thereafter, a dye is added as a safety measure to warn users and antimicrobial agents are added to protect the product during storage. The aqueous solution is then packaged in containers and distributed.

Like all containers of pesticides (a regulatory term referring to insecticides, plant. growth regulators, herbicides, etc.), empty containers for mepiquat chloride must be rinsed three times and disposed of with care. Such handling is a part of the normal routine for growers today. It would be desirable, however, if mepiquat chloride could be presented in a form and package that would reduce the time for and expense of container handling and disposal without adversely affecting the performance of the mepiquat chloride.

Cotton is a representative plant for describing the uses and effects of mepiquat chloride. Mepiquat chloride has the effect on cotton plants of stunting vegetative growth thereby forcing the plant to redirect its energies into fruit (cotton boll) production. With appropriate application of mepiquat chloride to plants that are beginning to exhibit excessive vegetative growth, cotton plant yields can be maintained or increased without harm to the plant.

Cotton plants have a predictable life cycle and growth period. Cotton plants emerge 7–10 days after the seeds are planted in a furrow. The cotton plant exhibits growth of a root system and the extension of plant height through stem and branch growth in a pattern referred to as "vegetative growth." Cotton plants that have directed the majority of the available plant energy to vegetative growth are referred to as "rank" cotton and produce little or no cotton bolls. Cotton that exhibits signs of going rank are readily visible by abnormal plant height relative to the boll loads. Mepiquat chloride is used to stop cotton from going rank by modifying the cotton plant's growth characteristics.

The branches off the main stem generally always extend from alternating sides of the stem. Each branch site is called a "node" with 5–7 nodes being formed above the cotyledon leaves before the first fruit bearing branch with true leaves is formed. Node counting starts at the bottom of the plant and extends up the main stem. The "internode length" is the distance between branch sites with a new node being formed roughly every three days. For purposes of measurement and comparison, the number of nodes and internode length above node 8 is generally used to eliminate interplant fruiting node variations because fruit bearing branches will necessarily have been formed by node 8.

Fruiting sites in cotton are referred to as "squares." Each fruit bearing branch will form three fruiting sites ("squares") with approximately six days between square formations on each branch. New squares and the beginning of reproductive growth in cotton plants are referred to as "pinhead" squares due to their barely visible size. After about three days, the square has grown to about the size of a match head and is a period in the plant cycle referred to as a "match head square." The match head square continues to grow about the size of an average adult fingernail before blooming ("early bloom"). Three days: later, a boll has formed beneath the bloom. Roughly thirty days after early bloom, the product boll is fully mature and ready for harvest. Overall, about 80% of the total cotton yield is set within the first 3 weeks of early bloom and 95% of the total yield is set within 5 weeks of early bloom.

Generally, mepiquat chloride is applied to cotton plants in one of two ways as a plant growth stunting agent. The method used until about 1987 was a single application of 8–16 ounces per acre of a 4.2 wt % solution at early bloom. This type of single treatments did control plant height although it was noticed that plant yields were occasionally reduced particularly if the plant was stressed during or after the application.

Since 1987, the trend has been to apply mepiquat chloride in a series of applications each having a lower dose than the single dose application. The first treatment occurs at match head square with a second treatment 7–14 days thereafter. Both treatments are made at a rate within the range from about 0–4 ounces of 4.2 wt % solution per acre with the specific application rate depending on whether the cotton plant was exhibiting signs of being stressed (no application), moderate growth (about 2 ounces of solution per acre), or vigorous growth (about 4 ounces of solution per acre). Thereafter, two additional treatments at 7–14 day intervals may be used with application rates extending up to about 8 ounces of 4.2 wt % mepiquat chloride solution with the specific application rate dependent on the amount of vegetative growth in the field.

Stunted plant growth can have the effect of increasing yields and boll retention but at the expense of the plant's ability to generate new growth. Such an effect can have broader ramifications, however, because the plant growing abilities hindered by mepiquat chloride are the same abilities that permit the plant's immune system to fight off diseases and to recover from insect damage to the plant tissues.

It would be desirable if the use of mepiquat chloride could be integrated into a system of treatment that would increase plant tissue mass in the roots, stems, and leaves to provide higher levels of nutrient transfer while, at the same time, restricting vegetative growth to enhance fruit production.

SUMMARY OF THE INVENTION

It is an objective of the invention to provide a method of making mepiquat chloride by a process that results in a solid form of mepiquat chloride in high yield and purity.

It is another objective of the invention to provide a tablet form of mepiquat chloride as well as a packaged forms of mepiquat chloride that avoids the handling of and need for containers subject to disposal regulations.

It is yet another objective of the invention to provide a system for growing cotton that promotes increased levels of plant mass for a more disease-resistant and faster recovering cotton plant with high levels of cotton yield.

In accordance with these and other objectives of the invention which will become apparent from the description herein, the process of making mepiquat chloride comprises contacting chloromethane with N-methylpiperidine in an anhydrous liquid solvent selected from the group consisting of acetone, methyl ethyl ketone, toluene, tetrahydrofuran, isopropanol, acetonitrile, N,N-dimethylformamide and methylene chloride for a time sufficient to precipitate solid mepiquat chloride; separating said solid mepiquat chloride from said solvent; and recovering said solid mepiquat chloride.

Packaged forms of mepiquat chloride include: (a) mepiquat chloride exhibiting the form of a powder having a purity of at least 98 wt % and being sealed within a pouch made from a material consisting essentially of a water soluble polymer; and (b) a core containing solid mepiquat chloride, and an outer layer completely surrounding said solid mepiquat chloride and comprising a water soluble polymer. Tablets may be prepared by compressing mepiquat chloride. If desired, the tablets may be coated with a material consisting essentially of a water soluble polymer.

A system for growing cotton comprises the steps of:

applying at least one plant growth hormone to at least one of: (a) a furrow for cotton plant seeds, (b) to a cotton plant bearing the first true leaves, (c) to a cotton plant at pinhead square, and (d) to a cotton plant at early bloom;

allowing cotton plants treated by said at least one plant growth hormone to exhibit vegetative and reproductive growth until mid-bloom; and applying an amount of mepiquat chloride that is effective to stunt the vegetative growth of said cotton plants.

By the present invention, the manufacture of mepiquat chloride provides a solid product in high yield with a high purity and a level of efficacy that surpasses mepiquat chloride made by the previous aqueous dimethylation process.

Mepiquat chloride exhibiting a purity of at least 98 wt % can be prepared using the present invention. The solid form permits the active ingredient to be formed into packaged forms that present a significantly reduced risk of contact through handling and fewer or no containers which require special handling procedures for disposal. Each of these aspects of the invention is used as a part of a system for growing cotton that provides a strong plant physiology and nutrient gathering network so that boll production and retention are maximized.

The system of the invention promotes high levels of plant mass in the roots, stems, and leaves during the early stages of plant growth. The increased plant mass provides a larger collection system for nutrients and minerals for the plant during the fruit-bearing stages of the life cycle when the mepiquat chloride is used to hinder vegetative growth.

DETAILED DESCRIPTION OF THE INVENTION

Mepiquat chloride is produced according to the invention in a batch process including the steps of: (a) contacting N-methylpiperidine with chloromethane in an anhydrous solvent selected from the group consisting of toluene, tetrahydrofuran, isopropanol, acetonitrile, N,N-dimethylformamide, methyl ethyl ketone, acetone, and mixtures thereof for the N-methylpiperidine and chloromethane at a temperature within the range from about 0°–200° C. for a time sufficient to produce at least 90% of the N-methylpiperidine to solid mepiquat chloride (N,N-dimethylpiperidinium chloride), (b) separating the mepiquat chloride from the anhydrous solvent, and (c) recovering solid mepiquat chloride having a purity of at least 98 wt %, preferably 99 wt %, more preferably 99.5 wt %. The solvent can be recovered and reused for a later batch, thereby increasing the economic operation of the process.

N-methylpiperidine is a restricted chemical available in purity levels of greater than 98% but which is substantially more expensive (about 400%) per unit weight than piperidine. In the present process, however, N-methylpiperidine can be readily methylated in anhydrous solvent in yields of greater than 90% to produce a solid precipitate product (100% retained on fast filter paper) having a degree of purity in excess of 99% without the formation of sodium chloride byproducts. More advantageously, use of an anhydrous solvent according to the invention permits recovery of a solid mepiquat chloride powder that exhibits a higher level of efficacy per unit weight of mepiquat chloride than the aqueous product commercially available to date. Such improved efficacy indicates that mepiquat chloride from the present invention will produce more consistent control over vegetative growth at the same application rates as mepiquat chloride made by the conventional aqueous dimethylation process using NaOH to maintain a basic solution pH. Solid mepiquat chloride powder according to the invention exhibits a white to light yellow color. Increased activity means that less active ingredient can be used to attain the same level of plant growth control or the same application rates will give more consistent control.

Chloromethane is a gas and can be contacted with the liquid phase by any of the conventional gas/liquid contact methods that is effective to transfer material in the gas into the liquid. The simplest and preferred method for the present invention is a tube extending below the surface of the liquid phase through which the chloromethane is passed. The tube exhibits a length sufficient to permit chloromethane to dissolve in the anhydrous solvent as a bubble of gas rises through the liquid. An array of distribution tubes and nozzles may be used, however, if desired.

The introduction rate of the chloromethane is desirably controlled to provide a reactor pressure of about 70 psi or less solely for economic reasons. Use of low reactor pressures reduces the cost of the reactor vessel. Higher reactor pressures from higher rates of chloromethane introduction may be used if the cost of the vessel is not a limiting factor.

It should be noted, however, that the methylation of N-methylpiperidine is an exothermic reaction and dependent on the introduction rate of the chloromethane. Bench top reactors will not generally need a cooling system if the heat can naturally dissipate through the reactor walls. When scaled up to larger reactor volumes, however, some form of cooling jacket or coils should be used whether on the outside of the reactor vessel or disposed within the reactor. The cooling rate and efficiency of the cooling system will be chosen by a chemical engineer exercising no more than the ordinary level of skill for one in this art as a part of an integrated process design at a given chloromethane feed rate.

The reactants and mepiquat chloride product of the present invention are quite stable against thermal degradation. Thus, the reaction temperature is functionally limited at the lower end of the operable range by the desired rate of reaction. Generally temperatures of greater than about 0° C. are needed for economic reaction rates. The highest practical temperature is limited by a combination of the vaporization temperature of the anhydrous solvent and the pressure rating of the reaction vessel. If acetone is used as the anhydrous solvent, a temperature of about 70° C. or less is preferred with a temperature within the range from about 40°–50° C. being most preferred to provide for some operational temperature variation during control over the process.

Anhydrous solvents useful as the medium for the present process include those solvents: (a) in which N-methylpiperidine and chloromethane are mutually soluble; (b) that are unreactive to N-methylpiperidine and chloromethane; and (c) in which mepiquat chloride exhibits a low solubility or is insoluble. Examples of suitable solvents exhibiting particularly high yields include those selected from the group consisting of acetone, methyl ethyl ketone, toluene, tetrahydrofuran, isopropanol, acetonitrile, N,N-dimethylformamide and methylene chloride. Isopropanol and acetone are particularly preferred solvents for their combinations of yield and handling safety with acetone being the most preferred.

Acetone, when used as a solvent in the preparation of mepiquat chloride, produces a product of a higher purity than heretofore known in the art. Acetone, while not a reactant, is able to dissolve impurities carried in the reactants. As such, dissolved impurities are washed out of the product filter cake with the solvent to leave a product of high purity.

Because the mepiquat chloride product is insoluble in the solvent, the product solid can be separated from the anhydrous solvent with most conventional equipment. Examples of suitable separation equipment include, inter alia, centrifuges, cylindrical filters (e.g., a Neutsche) equipped with appropriate filtration material, and plate and frame filters. The filtering apparatus is desirably made of a corrosion resistant material such as stainless steel. A recovered acetone wash during the separation process will assist in recovery of any unreacted N-methylpiperidine.

The product can be similarly dried with any of the conventional solids drying equipment. A vacuum drier made of stainless steel or glass lined carbon steel are particularly preferred.

Because mepiquat chloride powder is highly hygroscopic, contact with moisture or moisture laden atmospheres should be avoided to prevent caking or dissolution of the product. All separation, drying, forming, and packaging steps should be conducted under an inert atmosphere with a relative humidity that is as low as possible. Preferably, all handling steps where the solid mepiquat chloride product might be exposed to atmospheric or other moisture are conducted under a blanket of nitrogen although, e.g., any of the noble gases or carbon dioxide can also be used.

The recovered solid mepiquat chloride powder can be sealed in bulk, dissolved in water, packaged into disposable or recyclable containers, and sold in exactly the same manner as previously available from the aqueous methylation process. The solid form of mepiquat chloride resulting from the present invention provides the opportunity to package and use mepiquat chloride in a manner that poses less risk of accidental contact with less disposable materials than has previously been possible.

One packaging system for the high purity solid mepiquat chloride resulting from the present process of manufacture is to enclose the powder in a pouch of a water soluble sheet material. Examples of such materials include, inter alia, polyvinyl alcohol (PVA); cellulose-derived polymers such as methyl cellulose, hydroxypropyl cellulose, hydroxypropylmethyl cellulose, and mixtures thereof. A package made from a PVA inner pouch enclosed in a foil outer pouch is particularly preferred. The foil pouch is opened so the inner PVA pouch can be dropped into a tank or reservoir containing water thereby dissolving the PVA and releasing the mepiquat chloride into the tank.

Another embodiment is that the solid mepiquat chloride can be pressed into small briquettes or pellets which can then be encapsulated with a water soluble outer layer or coating in a level sufficient to fully encapsulate the briquette or pellet. Examples of suitable encapsulation materials include, inter alia, polyvinyl alcohol (PVA); cellulose-derived polymers such as methyl cellulose, hydroxypropyl cellulose, hydroxypropylmethyl cellulose, and mixtures thereof.

If desired, the solid mepiquat chloride powder can be suspended in a suitable anhydrous solvent or binder and coextruded with an outer encapsulation layer to make an encapsulated mepiquat chloride particle. Examples of suitable encapsulation materials include, inter alia, polyvinyl alcohol (PVA); cellulose-derived polymers such as methyl cellulose, hydroxypropyl cellulose, hydroxypropylmethyl cellulose, and mixtures thereof.

Regardless of the specific packaging method, one or more powdered additives can be added to the final package. Examples of suitable additives includes a water soluble solid dye to warn users that a spill of solids or the resulting aqueous solution contains mepiquat chloride. Suitable dyes include dyes approved as inert ingredients under the Food, Drug, and Cosmetic Act and listed in 40 Code of Federal Regulations §180.1001 which include, inter alia: FD & C Blue No. 1; Rhodamine B; methylene blue; methyl violet 2B; and red dye nos. 17, 40, and 48. The red and blue dyes are particularly preferred for visibility in aqueous solution.

If desired, solid feeding deterrent materials or emetics can be added as a deterrent against accidental or deliberate ingestion of the solid product. Particularly effective solid feeding deterrents include cucurbitacinous plant materials such as powdered roots from the buffalo gourd. An effervescent agent such as sodium bicarbonate can be added to the pelletized or briquette forms of the product as an aid to dissolutions and mixing after release in the spray tank or reservoir.

In general, there is no need to add spreader or sticker aids to mepiquat chloride although the presence of such aids will not adversely affect the stunting effects of mepiquat chloride.

Mepiquat chloride can be used in the application rates and at the periods in cotton plant growth exactly in the same manner as the conventional product made from the aqueous methylation process although somewhat less mepiquat chloride of the present invention is needed to achieve the same levels of plant growth control. Conventionally applied rates of mepiquat chloride are up to about 30 g/acre (12.4 g/acre) in individual application rates within the range from about 2.5 g/acre (1.0 g/hectare) for a 2 ounce/acre application of 4.2 wt % solution to 10 g/acre (4.1 g/hectare) for an 8 ounce/acre application of the same 4.2 wt % solution. Application rates for mepiquat chloride products of the invention will be slightly less (e.g., about 90–98%) than the conventional application rates to achieve the same stunting levels.

Crops on which mepiquat chloride of and from the present invention can be applied include cotton, potatoes, sweet potatoes, peanuts, grapes, corn, wheat, citrus, tomatoes, and onions.

One particular aspect of the present invention is to provide a system for growing cotton that includes sowing cotton seed in a furrow, applying a plant growth hormone containing growth fertilizer to the furrow around and on the seed, allowing the cotton plants to grow until mid bloom, and then applying mepiquat chloride to the plant at a rate sufficient to stunt vegetative growth. This combination of steps enhances early plant growth and plant mass (particularly root and stem growth) which translates into enhanced fruit set and retention. Thereafter, further vegetative growth is retarded by the mepiquat chloride in favor of fruit (boll) production. Because the plant growth was accelerated early in the life cycle, however, the plant assimilates larger quantities of nutrients which provides the plant immune system with a higher level of ability to resist diseases, recover from insect attack, and endure drought conditions.

Plant growth regulators suitable for the present invention and usable alone or in combination include those agents which enhance and encourage plant growth. Exemplary plant growth regulators include at least one of the 84 identified gibberillins with $GA_3$, $GA_4$, $GA_5$, $GA_7$ and $GA_9$ being preferred for the present invention, cytokinins (e.g., zeatin, kinetin, benzyladenine, dihydrozeatin, and isopentenyl adenine), auxins (e.g., indoleacetic acid (IAA), indolebutyric acid (IBA), and naphthalenacetic acid (NAA)), sodium orthonitrophenolate, sodium para-nitrophenolate, sodium 5-nitro-guaicolate, and polyhydroxycarboxylic acids of 2, 4, 5, and 6 carbon structures. Such plant growth regulators affect and alter plant metabolic processes to enhance plant growth. All such agents can be used according to the application rate specified on the product label.

While not wishing to bound by any particular theory, mepiquat chloride appears to be acting as an anti-plant growth hormone agent to stunt growth through some reaction or interference with the effects of plant growth hormones. Growing cotton according to the invention thus enhances early plant growth by adding growth regulating agents to the soil around the seeds and/or to the plant during its vegetative growth period to compensate for the interference later in the cycle by the mepiquat chloride.

Many fertilizers and growth regulating agents commercially available contain plant growth regulators. A particularly preferred plant growth regulating agent for use in the present invention is distributed by Micro Flo Company of Lakeland, Fla. USA under the trademark PGR-IV® which contains about 0.001 wt % of gibberillins, IBA, and other growth enhancing agents. Treatment of cotton seed furrows with PGR-IV® contemplates an application rate corresponding to an application rate of less than 20 g/acre (8 g/hectare), preferably less than 1 g/acre (0.4 g/hectare), and most preferably a rate within the range from about 30–300 mg/acre (12–121 mg/hectare) of plant growth regulating agents per application.

Mepiquat chloride is applied to the cotton plant in accordance with the invention at mid-bloom in the cotton plant life cycle although earlier application may be used for specific plants exhibiting early signs of going rank. Mid-bloom can be discerned by two tests measuring the same period: (a) 10 days after the appearance of 5 white blooms per 25 feet (7.6 m) of row or (b) an average internode length of about 3 inches (76 mm) as measured by the top four fully elongated nodes per plant. At mid-bloom, mepiquat chloride is applied at a rate within the range of 4–16 ounces (118–473 ml) of 4.2 wt % solution which corresponds to an application rate within the range of 5–20 g mepiquat chloride per acre (4.1–16.6 g/hectare). If vegetative growth is not adequately reduced, another application with the same application range can be used as long as the total application rate does not exceed about 32 ounces (946 ml) of 4.2 wt % solution per acre. Usually, no more than 24 ounces (710 ml) of 4.2 wt % solution per acre will be required.

EXAMPLES

Example 1

Mepiquat chloride is made in a small batch process by loading 4 liters of acetone into a reactor. One thousand grams of N-methylpiperidine is added to the solvent and sealed into a reactor. A total of 510 g of chloromethane (10% molar excess) is then introduced below the surface of the liquid in the reactor with a dip tube over a period of 2–6 hours. The introduction rate is controlled so that a pressure of 70 psi is not exceeded to stay within the pressure rating of the reactor vessel. The reaction was allowed to continue overnight so that the entire cycle took about 24 hours. Over 95% of the N-methylpiperidine was converted to mepiquat chloride which precipitated on the bottom of the reactor.

The solid mepiquat chloride was separated from the acetone solvent (which was recovered for reuse) by filtration. An acetone wash was used to remove any adsorbed impurities. The solid mepiquat chloride was dried with vacuum filtration and exhibited a purity of over 99.5%.

The proportions used in this example presented a molar ratio of chloromethane to N-methylpiperidine that was 1.1:1. In commercial operations where solvent recovery will return any unreacted chloromethane to the next batch, this ratio should be considered a minimum for maximum conversion with a molar ratio of chloromethane to N-methylpiperidine being at least 1:1, preferably within the range from about 1.05:1 to about 1.5:1.

Example 2

Batches of mepiquat chloride prepared in accordance with the inventive process are shown in Table 1. The solvents used and resulting products are compared.

TABLE 1

| SOLVENT | MEPIQUAT YIELD | EXPOSURE LIMITS TIME WEIGHTED AVG. ACGIH-TLV (PPM) |
|---|---|---|
| Heptane | 16 | 400 |
| Isopropanol | 80 | 400 |
| Toluene | 90 | skin 50 |
| Tetrahydro-furan | 94 | 200 |
| N,N-dimethyl formamide | 95 | skin 10 |
| Acetonitrile | 95 | 40 |
| Acetone | 96 | 750 |

Applicants have discovered that mepiquat chloride can be prepared in high yield by reacting N-methylpiperidine and chloromethane gases in certain solvents. An inert solvent such as heptane does not provide a medium exhibiting a yield as high as other solvents, even the noncyclic solvent isopropanol.

Isopropanol partially solubilizes mepiquat chloride, isopropanol has been discovered to be an extremely useful solvent in preparing mepiquat chloride in useful yields. It has been discovered that if the isopropanol mother liquor is recycled from batch to batch, yields increase.

Example 3

Solid mepiquat chloride dissolved in water to make a 4.2 wt % solution was compared to a 4.2 wt % aqueous solution sold under the trademark PIX®. PIX® is believed to be made by the conventional aqueous process of dimethylating piperidine under basic conditions maintained with NaOH.

The comparison tests were performed on a statistically significant number of cotton plants under controlled growing conditions. Active ingredient (AI) was applied to the cotton plant foliage at match head square with rates corresponding to 5 g/acre and 10 g/acre. This period in the life cycle of the cotton was chosen to identify any difference in effects with the cotton in a period of vigorous growth.

The designation SP represents a mepiquat chloride solution made from a soluble powder of mepiquat chloride as produced according to the invention. The results are reported in Table 2.

TABLE 2

| Measurement | 5 g AI/acre | | 10 g AI/acre | |
| --- | --- | --- | --- | --- |
| | SP | PIX® | SP | PIX® |
| Plant height (in cm, 14 days after treatment) | 76 | 82 | 76 | 78 |
| Improvement (%) | | 7.3 | | 2.6 |
| Change in plant height (in cm, 14 days after treatment) | 8 | 14.7 | 9.6 | 10.8 |
| Improvement (%) | | 45.6 | | 11.1 |
| Average internode length above node 8 (cm) | 3.9 | 4.6 | 3.9 | 4.2 |
| Improvement (%) | | 15.2 | | 0.7 |
| Plant height above node 8 (cm) | 36.7 | 44.3 | 39 | 38 |
| Improvement (%) | | 17.2 | | −2.6 |

From the results in Table 2, mepiquat chloride solutions made from the water soluble powders produced by the anhydrous process of the invention control plant height above node 8 better than the commercially available product believed to be made by the aqueous methylation process.

We claim:

1. A process for making mepiquat chloride comprising:
   contacting chloromethane with N-methylpiperidine in an anhydrous liquid solvent selected from the group consisting of acetone, methyl ethyl ketone, toluene, tetrahydrofuran, isopropanol, acetonitrile, N,N-dimethylformamide and methylene chloride for a time sufficient to precipitate solid mepiquat chloride in a yield of at least 80%;
   separating said solid mepiquat chloride from said solvent; and
   recovering said solid mepiquat chloride.

2. The process of claim 1 wherein the mepiquat chloride recovered exhibits a purity of at least 98 wt %.

3. The process of claim 1 wherein said solvent is acetone or isopropanol.

4. The process of claim 1 wherein chloromethane and N-methylpiperidine are contacted in said solvent in a molar ratio of chloromethane to N-methylpiperidine of at least 1:1.

5. The process of claim 1 wherein the mepiquat chloride recovered has a purity of at least 99 wt %.

6. A process as in claim 1 wherein the recovering step comprises:
   recovering mepiquat chloride solids having a purity of at least 99.5 wt %.

7. The process of claim 6 wherein said solvent is acetone.

8. The process of claim 1 wherein the separating step and the recovering step are each conducted under an atmosphere substantially free of moisture.

9. A process for making mepiquat chloride comprising:
   contacting chloromethane with N-methylpiperidine in acetone for a time sufficient to precipitate solid mepiquat chloride in a yield of at least 80%;
   separating said solid mepiquat chloride from said acetone; recovering said solid mepiquat chloride; and
   recycling said acetone.

10. The process of claim 9 wherein the mepiquat chloride recovered exhibits a purity of at least 98 wt %.

11. The process of claim 9 wherein said chloromethane is contacted with said N-methylpiperidine by bubbling chloromethane through N-methylpiperidine in acetone at a temperature of up to 70° C.

12. The process of claim 9 wherein the solid mepiquat chloride is separated from said acetone under an atmosphere consisting essentially of nitrogen.

13. The process of claim 1 further comprising:
   washing the separated solid mepiquat chloride with acetone, and
   recovering the acetone used for washing said solid mepiquat chloride for recycle to the contacting step.

14. Solid mepiquat chloride made by a process consisting essentially of:
   contacting chloromethane with N-methylpiperidine in acetone in the absence of NaOH for a time sufficient to precipitate solid mepiquat chloride in a yield of at least 80%;
   separating said solid mepiquat chloride from said acetone; and
   recovering said solid mepiquat chloride solids exhibiting a purity of at least 99.5 wt %.

15. A process according to claim 1 wherein greater than 90% of said N-methylpiperidine is converted into said mepiquat chloride.

16. A process according to claim 1 wherein said contacting is performed at a temperature of about 70° C. or less.

17. A process according to claim 1 wherein said contacting is performed at a temperature within the range of 40°–50° C.

18. A process according to claim 1 wherein said contacting is at a molar ratio of chloromethane to N-methylpiperidine of at least 1:1.

19. A process according to claim 18 wherein said contacting is at a molar ratio of chloromethane to N-methylpiperidine within the range of about 1.05:1 to about 1.5:1.

20. A process according to claim 1 wherein said separating and said recovering are conducted under an inert atmosphere.

21. A process according to claim 20 further comprising:
   sealing the separated mepiquat chloride in a package while under an inert atmosphere.

22. A process according to claim 1 further comprising:
   sealing the separated mepiquat chloride in a pouch made with a water soluble polymer.

23. A process as in claim 22 wherein said water soluble polymer is selected from the group consisting of polyvinyl alcohol and cellulose-derived polymers.

24. A process according to claim 23 wherein said pouch is enclosed in a foil outer pouch.

25. A process according to claim 1 further comprising:
   forming the separated mepiquat chloride into a solid pellet.

26. A process according to claim 25 further comprising:
   encapsulating said pellet with a water soluble outer coating.

27. A process as in claim 26 wherein said water soluble outer coating is selected from the group consisting of polyvinyl alcohol and cellulose-derived polymers.

28. A process as in claim 27 wherein said water soluble outer coating is selected from the group consisting of polyvinyl alcohol methyl cellulose, hydroxypropyl cellulose, hydroxypropylmethyl cellulose, and mixtures thereof.

* * * * *